United States Patent [19]

Heimann

[11] 4,031,624

[45] June 28, 1977

[54] EXTRACTION FORCEPS FOR UPPER MOLARS

[76] Inventor: Werner Heimann, Warendorfer Strasse 27, 4740 Oelde, Germany

[22] Filed: Jan. 15, 1976

[21] Appl. No.: 649,466

[52] U.S. Cl. .................................................. 32/62
[51] Int. Cl.² .......................................... A61C 3/14
[58] Field of Search ................................. 32/62, 61

[56] References Cited
UNITED STATES PATENTS 491,519   2/1893   Blake ...................................... 32/62

OTHER PUBLICATIONS

Hu—Friedy Manufacturing Co. Inc., 3118 N. Rockwell St., Chicago. P. 4, May 1, 1975.

Primary Examiner—Robert Peshock
Attorney, Agent, or Firm—Michael J. Striker

[57] ABSTRACT

An extraction forceps for upper molars is disclosed, including a pair of arms each having an end portion. Each end portion has a tooth-engaging jaw formed with two claws defining between themselves a recess. The arms are pivotally connected so that the jaws can pivot relative to one another in two laterally spaced planes about a pivot axis which extends skew to an imaginary line passing through the recesses of the two jaws.

10 Claims, 7 Drawing Figures

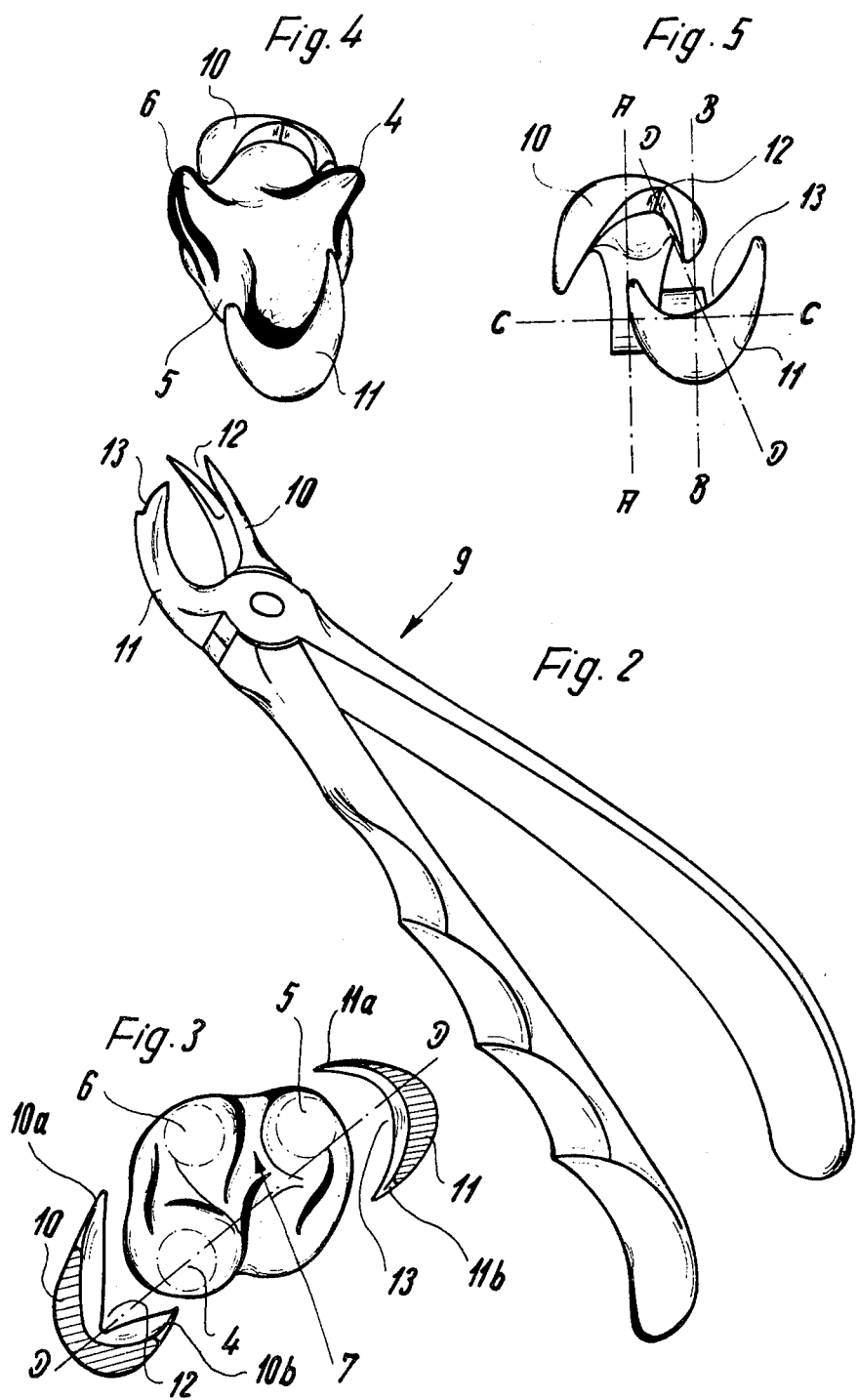

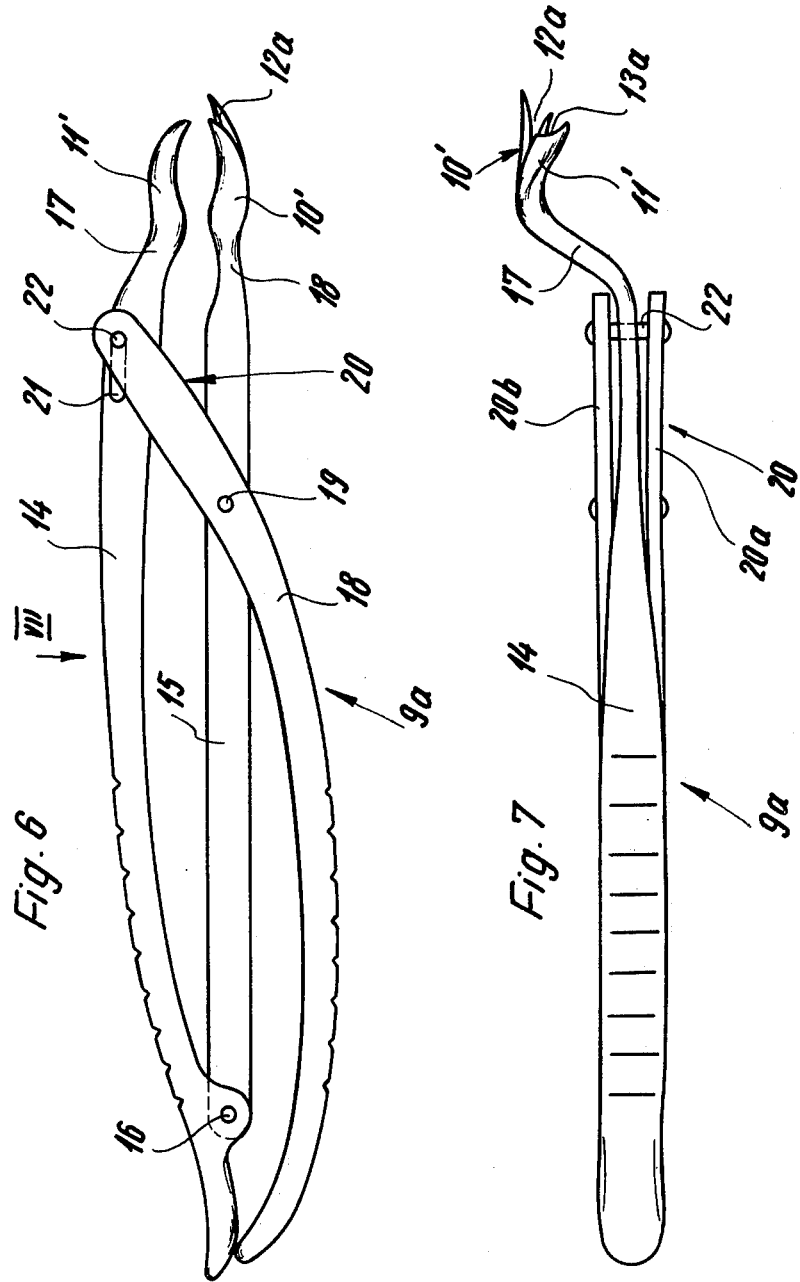

EXTRACTION FORCEPS FOR UPPER MOLARS

BACKGROUND OF THE INVENTION

This invention is concerned with extraction forceps for upper molars.

Forceps for this purpose are, of course, already known. They have jaws which are pivotable towards and away from one another in a common plane and which engage the tooth to be extracted at the inner and at the outer side.

This action has very substantial disadvantages which heretofore were never overcome.

One of these disadvantages resides in the fact that the upper molars are often shaped very differently at their inner and outer sides, and that the known forceps rarely assure completely reliable engagement of the tooth under these circumstances. This, then, leads to slipping of the forceps on, or even off, the tooth.

Furthermore, it has been found to be very disadvantageous to engage an upper molar-to-be-extracted from the inner and the outer side of the tooth. Such engagement necessarily results in stressing of the tooth at its narrowest cross-section where it is, evidently, most likely to break or shatter. This is facilitated by the fact that the tooth is already weakened by the attack which has in the first place lead to the need for performing the extraction. When the tooth does break on extraction, the removal of its root becomes very much more difficult and, in many instances, painful.

SUMMARY OF THE INVENTION

It is a general object of the invention to overcome the aforementioned disadvantages.

More particularly, it is an object of the invention to provide an improved extraction forceps for upper molars.

Still more specifically, it is an object to provide such an improved forceps which makes it possible to extract upper molars of all different anatomic shapes and which offers maximum assurance against breaking or shattering of the tooth being extracted.

In keeping with these objects, and with others which will become apparent hereafter, one feature of the invention resides in extraction forceps for upper molars which, briefly stated, comprise a pair of arms each having an end portion provided with a tooth-engaging jaw formed with claws defining a recess between themselves; and means connecting the arms for relative pivoting movement of the jaws in two laterally spaced planes about a pivot axis which extends skew to an imaginary line passing through the recesses of the jaws.

the novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIG. 2 is a perspective view of a forceps according to the invention;

FIG. 3 is a plan view of the grinding surface of an upper molar and shows in section the jaws of a forceps of the invention;

FIG. 4 shows the molar of FIG. 3 in a view from its root end, the forceps jaws being illustrated in engagement with the tooth;

FIG. 5 is a top plan view of the jaws of the novel forceps;

FIG. 6 is a side view illustrating a somewhat different embodiment of my forceps; and FIG. 7 is a view of FIG. 6 in the direction of the arrow VII.

DESCRIPTION OF THE PREFERRED EMBODIMENTS

Figure 1:
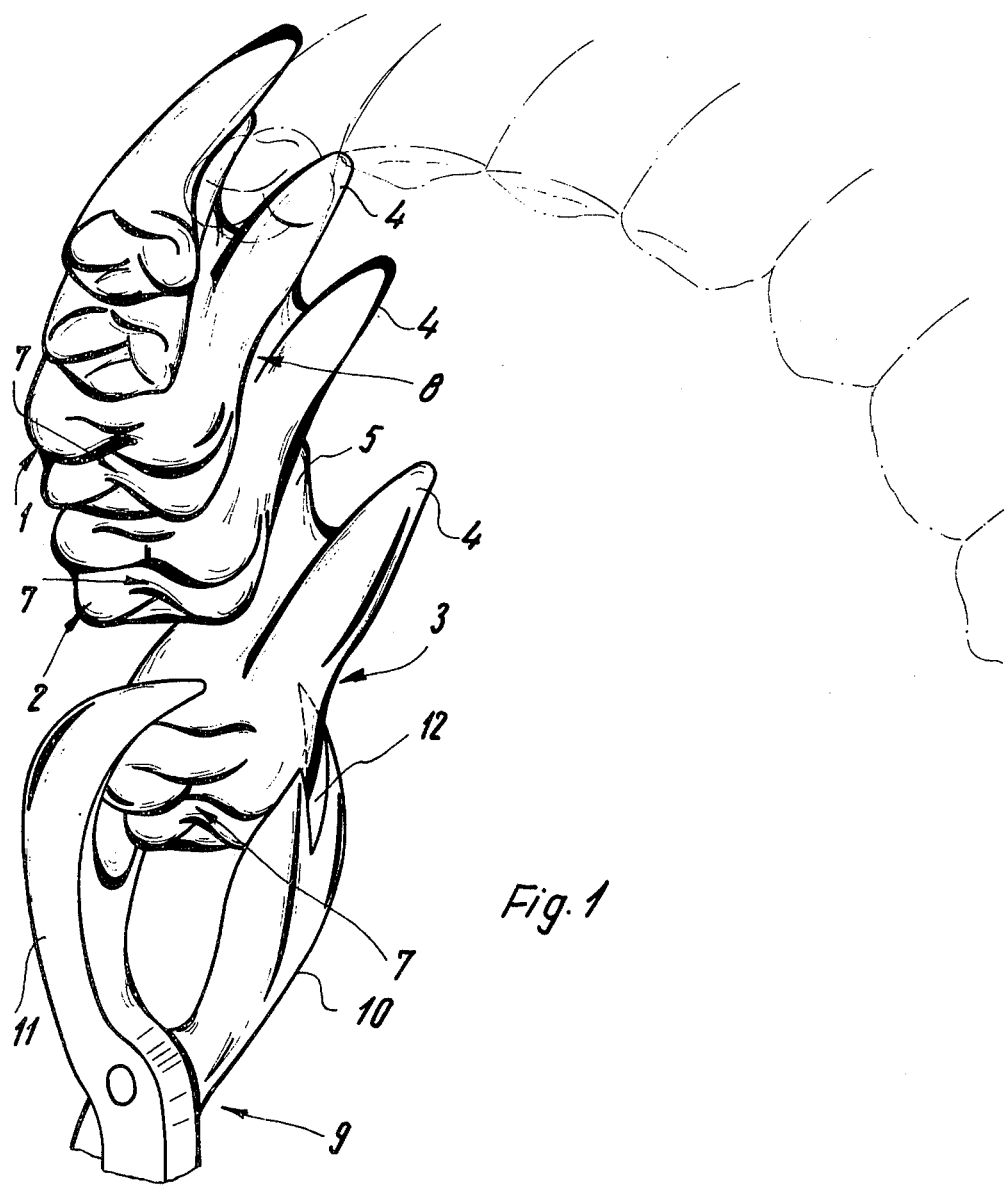
FIG. 1 is a perspective illustration, showing part of a row of upper teeth in broken lines, and showing in solid lines an extracted molar with a portion of a forceps according to the invention.

FIG. 1 shows part of a row of upper teeth, including molars 1, 2 and 3 at the right side. Each of the molars 1-3 has three roots 4, 5 and 6 which are most clearly shown in FIGS. 3 and 4. Of these, the root 4 is located rearwardly towards the gum, and the roots 5, 6 are located outwardly and rearwardly, respectively. This root location is the same in all upper molars and is completely independent of the shape of the tooth which can differ considerably from tooth to tooth.

Another aspect in which all upper molars resemble one another is in the fact that they taper towards their roots. This means that between adjacent upper molars, e.g., the molars 1 and 2, there will always be a more or less sizable space 8 upwardly of their grinding surfaces 7; this space is known as the interdental gap.

The invention is based on the presence of this interdental gap 8, in that the forceps 9 according to the invention (see FIG. 2) are so constructed that its two jaws 10 and 11 are constructed to be claw-shaped and their pivot planes A—A and B—B are transversely spaced from one another (FIG. 5). Furthermore, an imaginary connecting line D—D passing through the recesses of the jaws 10, 11 extends skew to the pivot axis C—C about which the arms of the forceps — and therefore the jaws 10, 11 — can pivot.

This construction of the novel forceps makes it possible to make use of the interdental gap 8, in that one jaw 10 engages the molar in the region of the root 4 whereas the other jaw 11 engages it in the region of the root 5. In so doing, the claws 10a, 10b of jaw 10 and the claws 11a, 11b of the jaw 11 enter the interdental gaps 8 and embrace the molar in close engagement.

The direction in which pressure is exerted on the molar by the jaws 10 and 11, is substantially diagonally of the tooth, from root 4 to root 5. This means that the pressure acts on the tooth in the region of its largest cross-section, i.e., where the tooth is best able to withstand the pressure. As a result, breaking or shattering of the tooth as a result of the extraction pressure is avoided, even if the tooth is weakened by the attack which necessitates its extraction.

The pressure on the tooth should be as uniform as possible, and the tooth should be embraced as closely as possible. To assure this, the present invention provides for the recess 12 in jaw 10 to be substantially V-shaped, whereas the recess 13 in jaw 11 is rounded, i.e., substantially semi-circular. It has been found that this configuration is especially beneficial, because it assures excellent contact of the jaws with the tooth, even if the tooth is slightly misshapen.

It should be noted, incidentally, that in all other respects the forceps can be of the type conventionally used, as seen in FIG. 2. It should also be noted that for the extraction of upper molars at the right-hand side of the mouth the forceps must be constructed as a "right-side" version, whereas a different "left-side" version must be provided for the molars at the left-hand side of the mouth. This "left-side" version will be mirror-reversed in the jaw construction, relative to the "right-side" version.

FIGS. 6 and 7 show a further embodiment of the invention which offers especially uniform pressure application from the handles to the jaws. The principle of the jaws is the same as in the preceding embodiment.

The forceps 9a in FIGS. 6 and 7 has two arms 14 and 15 which are pivoted together at a pivot 16 which is adjacent the rear end of the forceps. The front end regions of the arms 14, 15 are offset at 17 and 18 and are provided with the jaws 10', 11' having the recesses 12a, 13a.

A gripping lever 18 is pivoted to the arm 15 to be pivotable about an axis 19. The lever 18 has a bifurcated front end portion 20 which embraces the arms 14 and 15. A slot 21 is formed in arm 14 and a pin 22, which is mounted on and extends between the parts 20a, 20b of the end portion 20, extends through and is slidable in the slot 21. The outer surfaces of lever 18 and of arm 14 are serrated, knurled or otherwise roughened to facilitate gripping.

The invention offers the very important advantage that a molar to be extracted can now be engaged at its roots 4 and 5, so that the force applied to the tooth is diagonal of the same and passes through the area of greatest tooth cross-section. This very substantially reduces the possibility of breakage. Further, the entry of the claws into the interdental gaps provides for reliable gripping of the tooth and prevents slipping of the tool on, or even off, the tooth since the tooth is engaged in the region of roots 4 and 5 where, as experience has shown, there is a generally uniform rounding present in all upper molars, irrespective of other differences in shapes or sizes of the teeth.

It will be understood that each of the elements described above, or two or more together, may also find a useful application in other types of constructions differing from the types described above.

While the invention has been illustrated and described as embodied in an extraction forceps for upper molars, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Extraction forceps for upper molars, comprising a pair of arms each having an end portion provided with a tooth-engaging jaw formed with claws defining a recess between themselves; and means connecting said arms for relative pivoting movement of said jaws about a pivot axis which extends perpendicularly to planes of closure of said jaws, whereby the forces required for extraction of one of said upper molars are inclined with reference to a skew plane passing through the recesses of said jaws.

2. Extraction forceps as defined in claim 1, wherein one of said recesses is substantially V-shaped and the other recess is rounded.

3. Extraction forceps as defined in claim 1, said arms each also having a further end portion remote from the first-mentioned end portion; and furhter comprising pivot means pivotally coupling said arms to one another at said further end portion.

4. Extraction forceps as defined in claim 3, wherein one of further end portion projects beyond said pivot means and the other of said further end portions.

5. Extraction forceps as defined in claim 4, further comprising a gripping lever pivoted to the one arm having the other of said further end portions, said lever being displaceable relative to the other of said arms.

6. Extraction forceps as defined in claim 5, said other arm having a longitudinal slot, and said lever having a portion slidably received in said slot.

7. Extraction forceps as defined in claim 5, said lever having one end region pivoted to said one arm, and another end region which is bifurcated and straddles both of said arms.

8. Extraction forceps as defined in claim 5, said gripping lever having a finger-contacting surface provided with grip-facilitating surface contouring portions.

9. Extraction forceps as defined in claim 1, wherein said end portions of said arms are each provided with an offset.

10. Extraction forceps as defined in claim 1, wherein each of said jaws has two of said claws, at least some of said claws being adapted to enter into the interdental gaps at opposite sides of an upper molar.

* * * * *